United States Patent
Jaber et al.

(10) Patent No.: US 11,660,768 B2
(45) Date of Patent: May 30, 2023

(54) SURGICAL CLIPPER BLADE ASSEMBLIES WITH HYDROPHOBIC LAYERS AND METHODS OF USE

(71) Applicant: CareFusion 2200, Inc., San Diego, CA (US)

(72) Inventors: Anas Jaber, Schaumburg, IL (US); Gianluca Puliti, Mundelein, IL (US)

(73) Assignee: CareFusion 2200, Inc., San Diego, CA (US)

( * ) Notice: Subject to any disclaimer, the term of this patent is extended or adjusted under 35 U.S.C. 154(b) by 416 days.

(21) Appl. No.: 16/743,392

(22) Filed: Jan. 15, 2020

(65) Prior Publication Data

US 2020/0223078 A1  Jul. 16, 2020

Related U.S. Application Data

(60) Provisional application No. 62/792,596, filed on Jan. 15, 2019.

(51) Int. Cl.
*B26B 19/38* (2006.01)
*A61B 17/00* (2006.01)

(52) U.S. Cl.
CPC .......... *B26B 19/3846* (2013.01); *A61B 17/00* (2013.01); *B26B 19/3873* (2013.01);
(Continued)

(58) Field of Classification Search
None
See application file for complete search history.

(56) References Cited

U.S. PATENT DOCUMENTS

| 2,291,439 A | 7/1942 | Andis |
| 3,871,077 A | 3/1975 | Nissen et al. |

(Continued)

FOREIGN PATENT DOCUMENTS

| DE | 102011008314 A1 | 7/2012 |
| EP | 1295686 A1 | 3/2003 |

(Continued)

OTHER PUBLICATIONS

International Search Report of PCT/US2020/013635 dated May 20, 2020.

(Continued)

*Primary Examiner* — Hwei-Siu C Payer
(74) *Attorney, Agent, or Firm* — Dinsmore & Shohl LLP (57) ABSTRACT

Surgical clipper blade assemblies with hydrophobic coating layers and methods of use for hair removal from a skin area include using a surgical clipper blade assembly including a blade, a top surface, a bottom surface, a plurality of sidewalls disposed and extending between the top surface and the bottom surface, and an aperture configured to receive the blade, and a hydrophobic coating layer disposed on at least a portion of a top skin facing surface comprising the top surface and the blade. The surgical clipper blade assembly may include a plurality of ribs on the top surface, and the portion of the top skin facing surface may include the top surface, the blade, the plurality of ribs, or combinations thereof. During operation of the blade to remove hair from the skin area, the hydrophobic coating layer reduces friction forces and prevents risk of skin abrasions.

10 Claims, 5 Drawing Sheets

(52) U.S. Cl.
CPC ............... *A61B 2017/00734* (2013.01); *A61B 2017/00938* (2013.01)

(56) References Cited

U.S. PATENT DOCUMENTS

| | | | |
|---|---|---|---|
| 9,815,215 B2 | 11/2017 | Uit De Bulten et al. | |
| 11,318,628 B2 * | 5/2022 | Jaber | B26B 19/3853 |
| 2009/0106981 A1 | 4/2009 | Palmer et al. | |
| 2012/0110859 A1 | 5/2012 | Kammer | |
| 2014/0053412 A1 | 2/2014 | Carlucci et al. | |
| 2015/0183118 A1 * | 7/2015 | Roth | B26B 21/4081 |
| | | | 132/200 |
| 2016/0129601 A1 | 5/2016 | Kammer et al. | |
| 2016/0129602 A1 | 5/2016 | Mintz et al. | |
| 2016/0354939 A1 * | 12/2016 | Hill | C08J 7/16 |
| 2016/0361826 A1 | 12/2016 | Musallam | |
| 2020/0223078 A1 * | 7/2020 | Jaber | B26B 19/3873 |

FOREIGN PATENT DOCUMENTS

| | | |
|---|---|---|
| WO | WO 2017/120610 A2 * | 7/2017 |
| WO | WO 2021/108477 A1 * | 6/2021 |

OTHER PUBLICATIONS

International Search Report of PCT/US2020/013640 dated Apr. 20, 2020.

International Search Report of PCT/US2020/013636 dated Mar. 30, 2020.

\* cited by examiner

SURGICAL CLIPPER BLADE ASSEMBLIES WITH HYDROPHOBIC LAYERS AND METHODS OF USE

CROSS-REFERENCE

This application claims the benefit of and priority to U.S. Provisional Patent Application No. 62/792,596 titled Surgical Clipper Blade Assemblies with Hydrophobic Layers and Methods of Use, filed Jan. 15, 2019, the details of which are incorporated by reference.

TECHNICAL FIELD

The present disclosure generally relates to surgical clippers and methods of use, and more specifically, to surgical clipper blade assemblies with hydrophobic layers and methods of use.

BACKGROUND

Surgical clippers including blade assemblies assist with hair removal from the body of a patient in preparation of surgery or other medical procedure for which a skin area of the patient needs to be cleared of hair. Hair removal from the skin area may cause the skin to experience microscopic cuts and abrasions that may lead to contamination of a surgical wound and post-operative surgical site infection. Such surgical site infections may add to a number of post-operative hospital days for the patient and increase associated care costs. Use of surgical clippers by healthcare personnel for hair removal from the skin area may reduce a risk of cuts and abrasions compared to, for example, use of razers and shavers.

Accordingly, a need exists for alternative surgical clipper blade assemblies and methods of use to reduce a risk of surgical site infections.

SUMMARY

According to the subject matter of the present disclosure, a surgical clipper blade assembly may include a blade configured to remove hair from a skin area, a top surface, a bottom surface, a plurality of sidewalls disposed and extending between the top surface and the bottom surface, an aperture defined between an end portion of the top surface and an adjacent end portion of a sidewall, the aperture configured to receive the blade, a top skin facing surface comprising the top surface and the blade, and a hydrophobic coating layer disposed on at least a portion of the top skin facing surface.

In accordance with one embodiment of the present disclosure, a surgical clipper blade assembly may include a blade configured to remove hair from a skin area, a top surface, a bottom surface, a plurality of sidewalls disposed and extending between the top surface and the bottom surface, an aperture defined between an end portion of the top surface and an adjacent end portion of a sidewall, the aperture configured to receive the blade, a plurality of ribs in a rib pattern configuration disposed on the top surface, a top skin facing surface comprising the top surface, the blade, and the plurality of ribs, and a hydrophobic coating layer disposed on at least a portion of the top skin facing surface.

In accordance with another embodiment of the present disclosure, a method of using a surgical clipper blade assembly for hair removal from a skin area of a patient may include coupling the surgical clipper blade assembly to a body of a surgical clipper. The surgical clipper blade assembly may include a blade, a top surface, a bottom surface, a plurality of sidewalls disposed and extending between the top surface and the bottom surface, an aperture configured to receive the blade and defined between an end portion of the top surface and an adjacent end portion of a sidewall, and a hydrophobic coating layer disposed on at least a portion of a top skin facing surface comprising the top surface and the blade. The method may further include facing the top skin facing surface toward the skin area, and operating the blade through the body to remove hair from the skin area of the patient such that the hydrophobic coating layer reduces friction forces during blade operation and prevents risk of skin abrasions during blade operation.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Surgical clippers introduce friction with a skin area including hair for removal during use. Friction refers to a resistance that one surface or object encounters when moving over and with respect to another surface or object. Such surgical clipper friction may be caused by surface area contact with the skin area by a blade assembly of the surgical clipper. The friction may vary dependent on whether the skin area is dry or has been wetted with a skin preparation solution. In embodiments, such a skin preparation solution may include water and/or an antiseptic solution, such as one including chlorohexidine gluconate ("CHG"). With respect to the surgical clipper blade assemblies described herein, one or more skin contact areas may be coated with a hydrophobic layer to reduce such friction during use of the surgical clipper for hair removal from the skin area.

The hydrophobic layer disposed on the one or more skin contact areas of a surgical clipper blade assembly may include a hydrophobic, biocompatible coating configured to repel an aqueous solution from adhering to and being retained on the one or more skin contact areas of the surgical clipper blade assembly. Such repelling action through the hydrophobic layer assists with an increased agility and maneuverability and reduction of friction of the surgical clipper blade assembly with respect to use for hair removal with the skin area. In embodiments, the hydrophobic layer may be made of polytetrafluoroethene ("PTFE") or a similar polymer perfluoroalkoxy polymer resin ("PFA"), otherwise referable to as TEFLON as commercially available from The Chemours Company.

Figure 1:
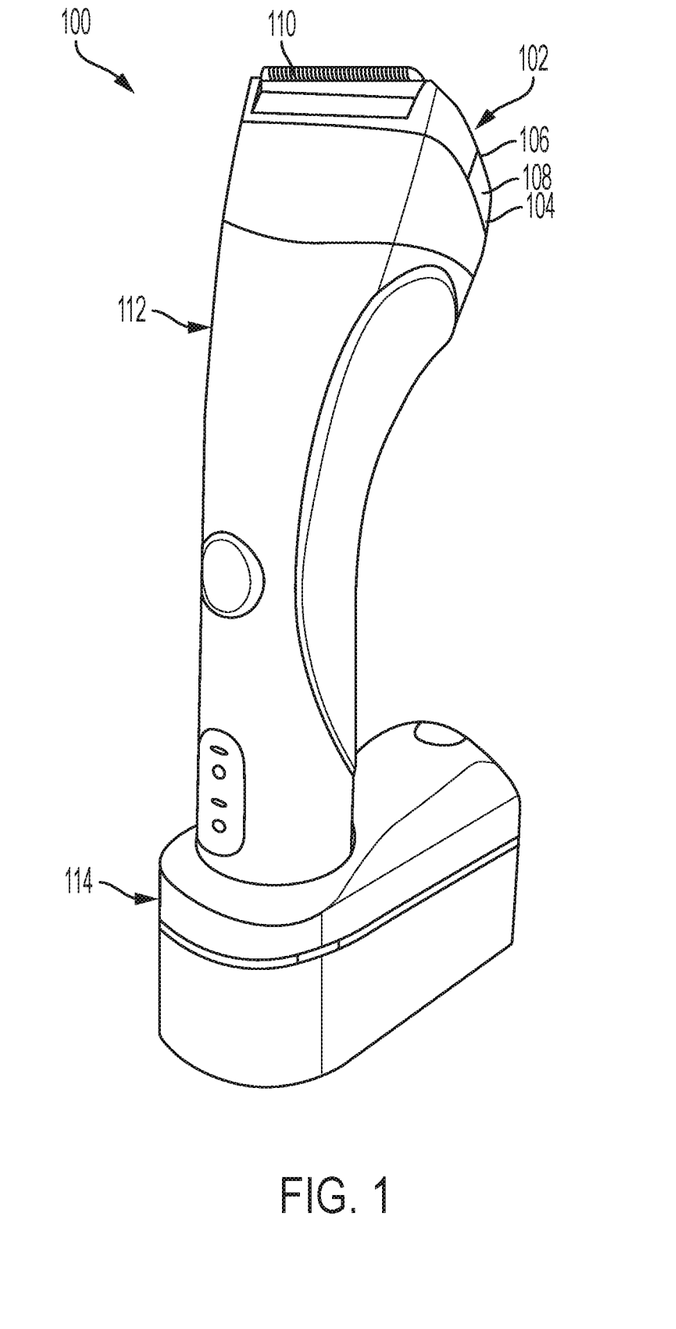
FIG. 1 illustrates an isometric view of a front facing portion of a surgical clipper including a surgical clipper blade assembly, according to one or more embodiments shown and described herein.

Referring initially to FIG. 1, a surgical clipper 100 includes a surgical clipper blade assembly 102. The surgical clipper 100 also includes a body 112 configured to attach at a top portion to the surgical clipper blade assembly 102 and a charging adaptor 114 configured to attach to a bottom portion of the body 112. The body 112 is an enclosure including an electrical motor and a rechargeable battery. The body 112 further includes an on/off switch, a lock button, and a charge indicator and may be include an indicator for a low battery level. In embodiments, the battery may be a lithium-ion battery, and the enclosure may be made of a plastic material such as such as acrylonitrile butadiene styrene ("ABS") plastic.

The charging adaptor 114 is configured to power and charge the battery of the body 112. After the battery of the body 112 is charged, the body 112 may be removed from the charging adaptor 114 and used to electronically operate the attached surgical clipper blade assembly 102 to remove hair from a skin area of a patient.

In embodiments, the surgical clipper blade assembly 102 may be removably attached with respect to the top portion of the body 112. In some embodiments, after use for hair removal, the surgical clipper blade assembly 102 may be disposed and the body 112 may later be used with another surgical clipper blade assembly 102. In other embodiments, the surgical clipper blade assembly 102 may be integrally attached to the top portion of the body 112 or be removably attached and used for a plurality of uses prior to disposal.

The surgical clipper blade assembly 102 includes a top skin facing surface configured to contact the skin area. The top skin facing surface of the surgical clipper blade assembly 102 includes a top surface 106 and a blade 110. The surgical clipper blade assembly 102 further includes a bottom surface 104 and a plurality of sidewalls 108 disposed and extending between the bottom surface 104 and the top surface 106. In embodiments, the blade 110 including a plurality of blade edges configured to remove hair is retained by an opening defined between an end portion of the top surface 106 and an adjacent end portion of a sidewall 108. The blade 110 is configured to be operated by the body 112 to remove hair from the skin area of the patient. The blade 110 may be configured for general purpose hair removal, removal of thick coarse hair from a scalp area or other area, and/or hair removal from sensitive skin areas such as the perineal area of a patient. In an embodiment, the blade 110 is made of stainless steel, and the top surface 106, the bottom surface 104, and the sidewalls 108 are made of a plastic material such as ABS plastic.

Figure 2:
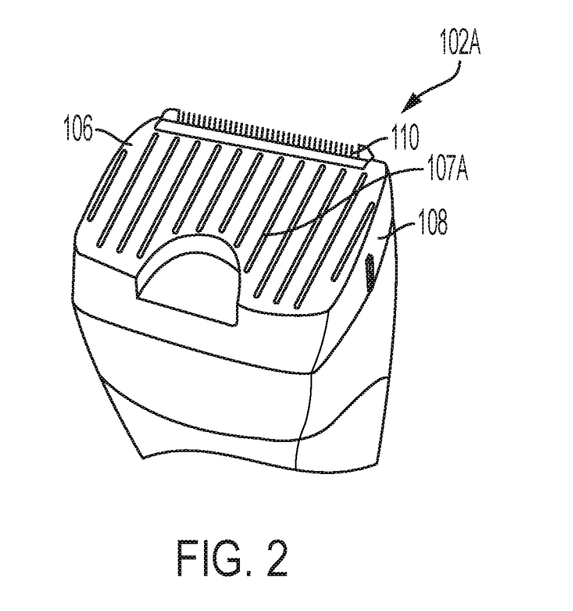
FIG. 2 illustrates an embodiment of a rear facing portion of the surgical clipper blade assembly of FIG. 1 including an angled, top skin facing surface with a plurality of ribs in a rib pattern configuration.
Figure 3:
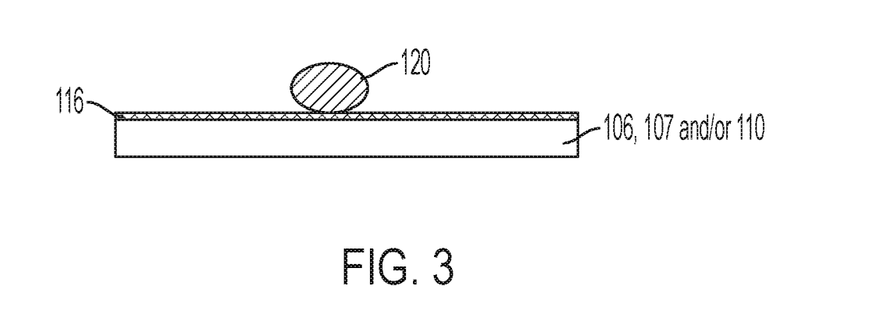
FIG. 3 schematically illustrates a hydrophobic coating layer on the surgical clipper blade assembly of FIG. 1 or 2, according to one or more embodiments shown and described herein.

Referring to FIGS. 2-3, the top surface 106 may additionally include a plurality of ribs 107 in a rib pattern configuration, such as the surgical clipper blade assembly 102A including the plurality of ribs 107A in FIG. 2. The plurality of ribs 107A are depicted as a straight rib pattern configuration. The plurality of ribs 107 may be made the plastic material such as ABS plastic. The plurality of ribs 107 may be formed from the mold forming the top surface 106, the bottom surface 104, and the sidewalls 108 of the surgical clipper blade assembly 102. By way of example, and not as a limitation, the plurality of ribs 107 may be etched or molded on the top surface 106 of the surgical clipper blade assembly 102.

With respect to FIG. 3, a hydrophobic coating layer 116 may be coated on top of the top surface 106, the plurality of ribs 107, and/or the blade 110 of a surgical clipper blade assembly 102 to repel an aqueous solution 120, such as water, from adhering to the coated top surface 106, the plurality of ribs 107, and/or the blade 110. It is to be understood that ribs pattern configurations other than those described herein may be coated with the hydrophobic coating layer 116 and are within the scope of this disclosure. In embodiments, the hydrophobic coating layer 116 is coated on one or more surfaces of the plurality of ribs 107 and may be coated on the top surfaces of the plurality of ribs 107.

In an embodiment, the hydrophobic coating layer 116 of FIG. 3 may be applied to only the top surface 106 of FIG. 2. Additionally or alternatively, the hydrophobic coating layer 116 of FIG. 3 may be applied to the plurality of ribs 107A of FIG. 2. In other additional or alternative embodiments, the hydrophobic coating layer 116 of FIG. 3 may be applied to the blade 110 of FIG. 2.

In one or more embodiments, the surgical clipper blade assembly 102 may include a total surface area in a range from about 10 cm$^2$ to about 11 cm$^2$ and a plurality of ribs 107 disposed on the top surface 106 that have a surface area in a range of from about 1.85 cm$^2$ to about 2.56 cm$^2$. As a non-limiting example, the surgical clipper blade assembly 102 may include a total surface area of about 10 cm$^2$ and a plurality of ribs 107 that have a surface area of about 2 cm$^2$. Coating of the hydrophobic coating layer 116 on the plurality of ribs 107 thus provides for a coating of approximately 20% of the total surface area of the surgical clipper blade assembly 102. In embodiments, the hydrophobic coating layer 116 may be disposed on the plurality of ribs 107 on the top surface 106 and cover a percentage in a range of between 16.8% to 25.6% of the total surface area of the surgical clipper blade assembly 102.

Figure 4:
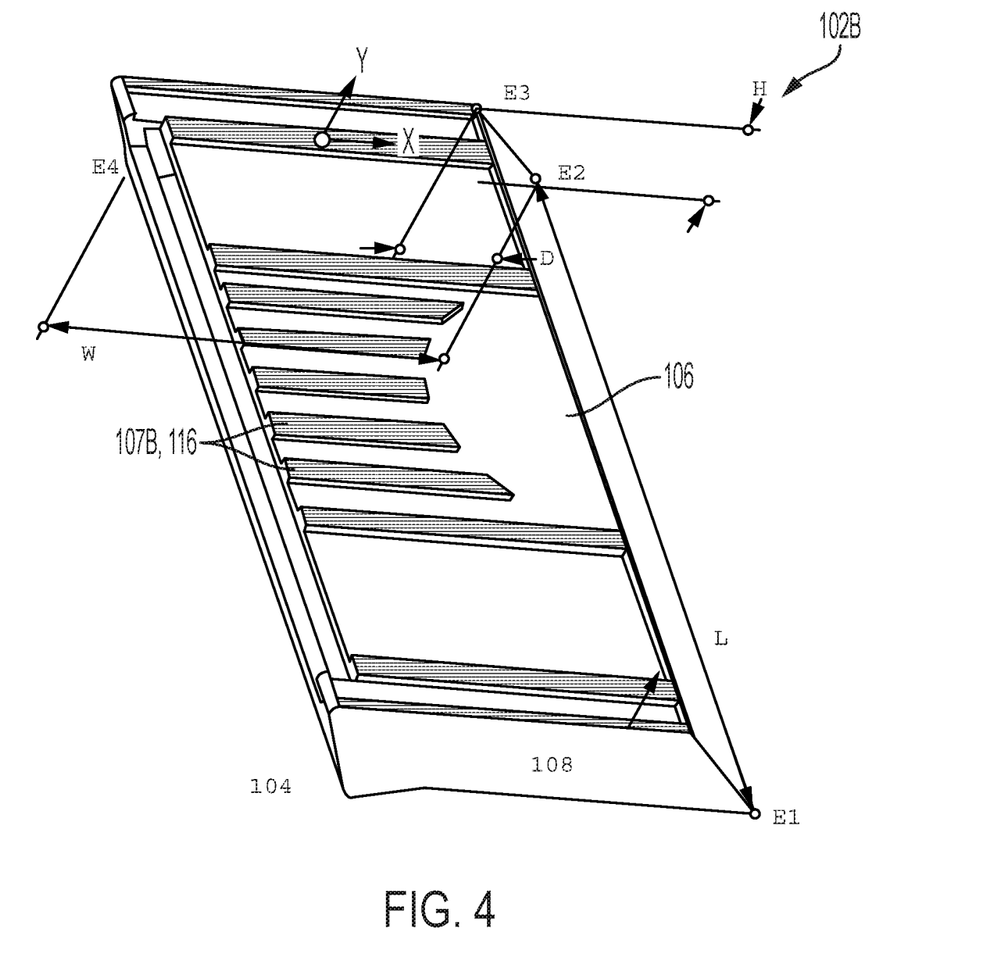
FIG. 4 illustrates another embodiment of the surgical clipper blade assembly of FIG. 1 including a top skin facing surface including a plurality of ribs in another rib pattern configuration and coated with the hydrophobic coating layer of FIG. 3, according to one or more embodiments shown and described herein.

Referring to FIG. 4, another embodiment of the surgical clipper blade assembly 102 of FIG. 1 is shown as surgical clipper blade assembly 102B. The surgical clipper blade assembly 102B includes a top skin facing surface having a plurality of ribs 107B disposed on the top surface 106 in another rib pattern configuration. The plurality of ribs 107B are coated with the hydrophobic coating layer 116 of FIG. 3. In an XY coordinate plane including an X-axis and a Y-axis, FIG. 4 shows a length L between endpoints E1 and E2 at bottom edges of the bottom surface 104, a vertical distance H along the Y-axis between endpoints E2 and E3 at a top edge of the top surface 106, a horizontal distance D along the X-axis between endpoints E2 and E3, and a width W between endpoints E2 and E4 at an opposing bottom edge of the bottom surface 104. In an embodiment of FIG. 4, the length L may be approximately 48.30 mm, a radius of endpoint E2 may be 0.20 mm, a radius of endpoint E3 may be 0.50 mm, the vertical distance H may be 6 mm, the horizontal distance D may be 6.50 mm, and the width W may be 25.32 mm. Endpoint E2 may be angled with respect to endpoint E3 at about 42.71 degrees. In embodiments, the width W may be in a range of from about 40% to about 60% of the length L, and the vertical distance D may be in a range of from about 80% to 100% of the horizontal distance D and in a range of from about 5% to 20% of the length L.

Figure 5:
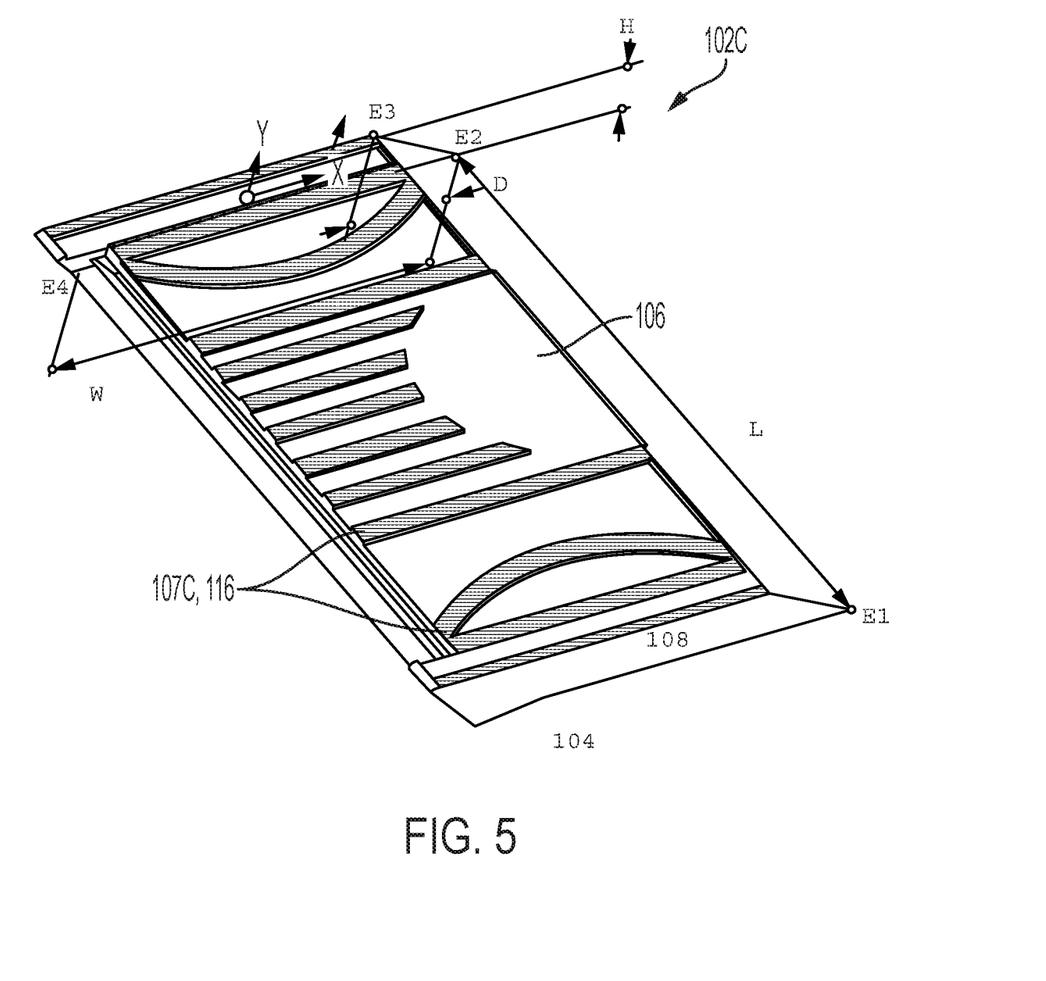
FIG. 5 illustrates another embodiment of the surgical clipper blade assembly of FIG. 1 including a top skin facing surface including a plurality of ribs in yet another rib pattern configuration and coated with the hydrophobic coating layer of FIG. 3, according to one or more embodiments shown and described herein.

Referring to FIG. 5, yet another embodiment of the surgical clipper blade assembly 102 of FIG. 1 is shown as surgical clipper blade assembly 102C. The surgical clipper blade assembly 102C includes a top skin facing surface having a plurality of ribs 107C disposed on the top surface 106 in yet another rib pattern configuration. The plurality of ribs 107C are coated with the hydrophobic coating layer 116 of FIG. 3. In an XY coordinate plane including an X-axis and a Y-axis, FIG. 5 shows a length L between endpoints E1 and E2 at bottom edges of the bottom surface 104, a vertical distance H along the Y-axis between endpoints E2 and E3 at a top edge of the top surface 106, a horizontal distance D along the X-axis between endpoints E2 and E3, and a width W between endpoints E2 and E4 at an opposing bottom edge of the bottom surface 104. In an embodiment of FIG. 5, the length L may be approximately 48.30 mm, a radius of endpoint E2 may be 0.20 mm, a radius of endpoint E3 may be 0.50 mm, the vertical distance H may be 6 mm, the horizontal distance D may be 6.50 mm, and the width W may be 25.32 mm. Similarly to FIG. 4, endpoint E2 may be angled with respect to endpoint E3 at about 42.71 degrees. Further similar to FIG. 4, in embodiments, the width W may be in a range of from about 40% to about 60% of the length L, and the vertical distance D may be in a range of from about 80% to 100% of the horizontal distance D and in a range of from about 5% to 20% of the length L.

Figure 6:
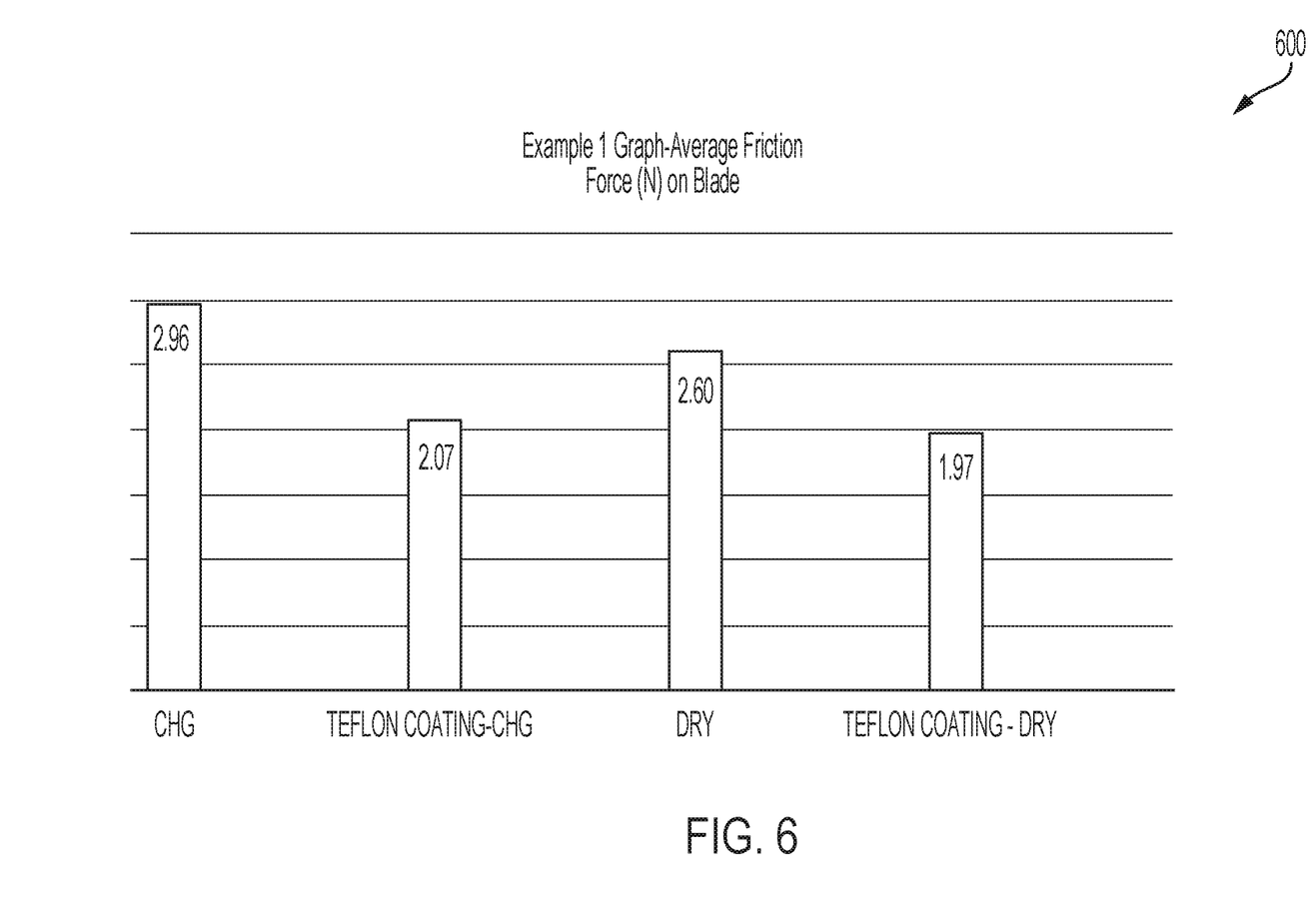
FIG. 6 illustrates a graphical view of data from friction study results of use of a surgical clipper blade assembly of FIG. 1 with and without the hydrophobic coating layer of FIG. 3 as a Teflon coating, according to one or more embodiments shown and described herein.

Referring to FIG. 6, a graph 600 is shown illustrating friction study results of use of a surgical clipper blade assembly 102 of FIG. 1 with and without the hydrophobic coating layer 116 of FIG. 3 applied as a TEFLON coating. The friction study used a measurement of a handle load and 0.5 lb weight to equal 3.5 N, and all readings were recorded in Newton Force (N). A surgical clipper blade assembly 102 without the TEFLON coating and a surgical clipper blade assembly 102 with the TEFLON coating was moved with respect to and facing a CHG-wetted skin contact area to which CHG was applied to record five readings for each assembly respectively for three users. A surgical clipper blade assembly 102 without the TEFLON coating and a surgical clipper blade assembly 102 with the TEFLON coating was further moved with respect to and facing a dry skin contact area to record five readings for each assembly respectively for the three users. Results from the friction study are set forth below in Table 1.

Table 1 shows that the surgical clipper blade assembly 102 without the TEFLON coating moved with respect to and facing the CHG-wetted skin contact area to which CHG was applied to record five readings for each assembly respectively for three users. The following five readings were respectively recorded for User 1 for the CHG-wetting application without TEFLON coating: 2.9 N, 2.95 N, 3 N, 2.8 N, and 2.8 N, which resulted in a mean value of 2.890 N, a standard deviation (Std in Table 1) of 0.089, a minimum reading value (Min in Table 1) of 2.8 N, and a maximum reading value (Max in Table 1) of 3 N. The following five readings were respectively recorded for User 2 for the CHG-wetting application without TEFLON coating: 3 N, 3.1 N, 3.1 N, 3 N, and 2.8 N, which resulted in a mean value of 3.000 N, a standard deviation of 0.122, a minimum reading value of 2.8 N, and a maximum reading value of 3.1 N. The following five readings were respectively recorded for User 3 for the CHG-wetting application without TEFLON coating: 3.1 N, 3.2 N, 3.1 N, 2.8 N, and 2.8 N, which resulted in a mean value of 3.000 N, a standard deviation of 0.187, a minimum reading value of 2.8 N, and a maximum reading value of 3.2 N. The average friction (Avg in Table 1) between Users 1-3 over these respective five readings for the CHG-wetting application without TEFLON coating is 2.96 N.

Table 1 further shows that the surgical clipper blade assembly 102 with the TEFLON coating moved with respect to the CHG-wetted skin contact area to which CHG was applied to record five readings for each assembly respectively for three users. The following five readings were respectively recorded for User 1 for the CHG-wetting application with TEFLON coating: 2.4 N, 2.2 N, 2.1 N, 2.1 N, and 2 N, which resulted in a mean value of 2.160 N, a standard deviation of 0.152, a minimum reading value of 2 N, and a maximum reading value of 2.2 N. The following five readings were respectively recorded for User 2 for the CHG-wetting application with TEFLON coating: 2.1 N, 2 N, 1.9 N, 2 N, and 2 N, which resulted in a mean value of 2.000 N, a standard deviation of 0.071, a minimum reading value of 1.9 N, and a maximum reading value of 2 N. The following five readings were respectively recorded for User 3 for the CHG-wetting application with TEFLON coating: 1.9 N, 2 N, 2.1 N, 2.1 N, and 2.2 N, which resulted in a mean value of 2.060 N, a standard deviation of 0.114, a minimum reading value of 1.9 N, and a maximum reading value of 2.2 N. The average friction between Users 1-3 over these respective five readings for the CHG-wetting application with TEFLON coating is 2.07 N.

Table 1 also shows that the surgical clipper blade assembly 102 without the TEFLON coating moved with respect to and facing the dry skin contact area to record five readings for each assembly respectively for three users. The following five readings were respectively recorded for User 1 for the dry application without TEFLON coating: 2.6 N, 2.5 N,

TABLE 1

| # | CHG | | | Teflon Coating- CHG | | | Dry | | | Teflon Coating- Dry | | |
| --- | --- | --- | --- | --- | --- | --- | --- | --- | --- | --- | --- | --- |
| | User 1 | User 2 | User 3 | User 1 | User 2 | User 3 | User 1 | User 2 | User 3 | User 1 | User 2 | User 3 |
| 1 | 2.9 | 3 | 3.1 | 2.4 | 2.1 | 1.9 | 2.6 | 2.4 | 2.5 | 1.9 | 2 | 1.8 |
| 2 | 2.95 | 3.1 | 3.2 | 2.2 | 2 | 2 | 2.5 | 2.5 | 2.45 | 1.9 | 2 | 1.9 |
| 3 | 3 | 3.1 | 3.1 | 2.1 | 1.9 | 2.1 | 2.5 | 2.7 | 2.7 | 1.8 | 2.1 | 2.2 |
| 4 | 2.8 | 3 | 2.8 | 2.1 | 2 | 2.1 | 2.7 | 2.7 | 2.8 | 1.8 | 2.1 | 2.1 |
| 5 | 2.8 | 2.8 | 2.8 | 2 | 2 | 2.2 | 2.6 | 2.65 | 2.75 | 2 | 1.9 | 2.1 |
| Mean (N) | 2.890 | 3.000 | 3.000 | 2.160 | 2.000 | 2.060 | 2.580 | 2.590 | 2.640 | 1.880 | 2.020 | 2.020 |
| Std | 0.089 | 0.122 | 0.187 | 0.152 | 0.071 | 0.114 | 0.084 | 0.134 | 0.156 | 0.084 | 0.084 | 0.164 |
| Min | 2.8 | 2.8 | 2.8 | 2 | 1.9 | 1.9 | 2.5 | 2.4 | 2.45 | 1.8 | 1.9 | 1.8 |
| Max | 3 | 3.1 | 3.2 | 2.2 | 2 | 2.2 | 2.7 | 2.7 | 2.8 | 2 | 2.1 | 2.2 |
| Avg | | 2.96 | | | 2.07 | | | 2.60 | | | 1.97 | |

2.5 N, 2.7 N, and 2.6 N, which resulted in a mean value of 2.580 N, a standard deviation of 0.084, a minimum reading value of 2.5 N, and a maximum reading value of 2.7 N. The following five readings were respectively recorded for User 2 for the dry application without TEFLON coating: 2.4 N, 2.5 N, 2.7 N, 2.7 N, and 2.65 N, which resulted in a mean value of 2.590 N, a standard deviation of 0.134, a minimum reading value of 2.4 N, and a maximum reading value of 2.7 N. The following five readings were respectively recorded for User 3 for the dry application without TEFLON coating: 2.5 N, 2.45 N, 2.7 N, 2.8 N, and 2.75 N, which resulted in a mean value of 2.650 N, a standard deviation of 0.156, a minimum reading value of 2.45 N, and a maximum reading value of 2.8 N. The average friction between Users 1-3 over these respective five readings for the dry application without TEFLON coating is 2.60 N.

Table 1 additionally shows that the surgical clipper blade assembly 102 with the TEFLON coating moved with respect to and facing the dry skin contact area to record five readings for each assembly respectively for three users. The following five readings were respectively recorded for User 1 for the dry application with TEFLON coating: 1.9 N, 1.9 N, 1.8 N, 1.8 N, and 2 N, which resulted in a mean value of 1.880 N, a standard deviation of 0.084, a minimum reading value of 1.8 N, and a maximum reading value of 2 N. The following five readings were respectively recorded for User 2 for the dry application with TEFLON coating: 2 N, 2 N, 2.1 N, 2.1 N, and 1.9 N, which resulted in a mean value of 2.020 N, a standard deviation of 0.084, a minimum reading value of 1.9 N, and a maximum reading value of 2.1 N. The following five readings were respectively recorded for User 3 for the dry application with TEFLON coating: 1.8 N, 1.9 N, 2.2 N, 2.1 N, and 2.1 N, which resulted in a mean value of 2.020 N, a standard deviation of 0.164, a minimum reading value of 1.8 N, and a maximum reading value of 2.2 N. The average friction between Users 1-3 over these respective five readings for the CHG-wetting application without TEFLON coating is 1.97 N.

Referring again to FIG. 6, the graph 600 shows the average (Avg) results from TABLE 1. The graph 600 depicts that use of a surgical clipper blade assembly 102 without the TEFLON coating and moved with respect to and facing a skin contact area to which CHG was applied resulted in an average force of 2.96 N. Further, the graph 600 depicts that use of a surgical clipper blade assembly 102 with the TEFLON coating and moved with respect to and facing a skin contact area to which CHG was applied resulted in an average force of 2.07 N, which show a reduction in friction when compared to the average force of 2.96 N of the surgical clipper blade assembly 102 without the TEFLON coating used with respect to and facing the CHG-wetted skin contact area.

The graph 600 further depicts that use of a surgical clipper blade assembly 102 without the TEFLON coating and moved with respect to and facing a dry skin contact area resulted in an average force of 2.60 N. Further, the graph 600 depicts that use of a surgical clipper blade assembly 102 with the TEFLON coating and moved with respect to and facing a dry skin contact area resulted in an average force of 1.97 N, which shows a reduction in friction when compared to the average force of 2.60 N of the surgical clipper blade assembly 102 without the TEFLON coating used with respect to and facing the dry skin contact area. Thus, use of a surgical clipper blade assembly 102 with respect to and facing a dry skin contact area results in less friction than with respect to and facing a CHG-wetted skin contact area, and use of a surgical clipper blade assembly 102 including the TEFLON coating to contact the dry or CHG-wetted skin contact area respectively results in less friction than use of a surgical clipper blade assembly 102 that does not include the TEFLON coating.

A method of using the surgical clipper blade assembly for hair removal from a skin area of a patient may include coupling the surgical clipper blade assembly to the body 112 of a surgical clipper 100. The surgical clipper blade assembly 102 includes, as described herein, the blade 110, the top surface 106, the bottom surface 104, the plurality of sidewalls 108 disposed and extending between the top surface 106 and the bottom surface 104, an aperture configured to receive the blade 110 and defined between an end portion of the top surface 106 and an adjacent end portion of a sidewall 108, and a hydrophobic coating layer 116 disposed on at least a portion of a top skin facing surface comprising the top surface 106 and the blade 110. The method includes facing the top skin facing surface of the surgical clipper blade assembly 102 with respect to and toward the skin area, and operating the blade 110 through the body 112 to remove hair from the skin area of the patient such that the hydrophobic coating layer 116 reduces friction forces during blade operation and prevents risk of skin abrasions during blade operation.

As described above, the hydrophobic coating layer 116 may be made of polytetrafluoroethene (PTFE) or perfluoroalkoxy polymer resin (PFA) (e.g., TEFLON). The portion of the top skin facing surface coated by the hydrophobic coating layer 116 may include the top surface 106, the blade 110, or both. The surgical clipper blade assembly 102 may further include a plurality of ribs 107 in a rib pattern configuration disposed on the top surface 106, as described herein, such that the top skin facing surface further includes the plurality of ribs 107. In such embodiments, the portion of the top skin facing surface coated by the hydrophobic coating layer 116 may include the plurality of ribs 107, the top surface 106, the blade 110, or combinations thereof.

As described herein, the body 112 of the surgical clipper 100 is configured to electronically operate the blade 110. The body 112 includes the enclosure housing an electrical motor and a battery, which battery is configured to be rechargeable through coupling of the body 112 to the charging adaptor 114. The body 112 of the surgical clipper 100 further may include a charge indicator configured to indicate a low battery level of the battery below a predefined threshold. The method may include triggering an alarm through the charge indicator of the low battery level, coupling the body to the charging adaptor, and recharging the battery. The alarm may be a visual, audio, or tactile alarm. Such a visual alarm may be an LED light that may, for example, red to indicate the low battery level.

In the embodiments described herein, use of the hydrophobic coating layer 116 disposed on at least a portion of a top skin facing surface configured to contact the skin area, the portion including the top surface 106, the blade 110, and/or the plurality of ribs 107, results in a reduction of friction forces when using the surgical clipper blade assembly 102 for hair removal at a skin area of a patient than may result without the hydrophobic coating layer 116. Such reduced friction forces aids to reduce a risk of skin nicking that could lead to surgical site infections, aids is the agility and maneuverability of the surgical clipper blade assembly 102 on the skin area, and aids to reduce stickiness and adherence of aqueous solutions from the skin area to the surgical clipper blade assembly 102.

Clause 1. In an embodiment, a surgical clipper blade assembly may include a blade configured to remove hair from a skin area, a top surface, a bottom surface, a plurality of sidewalls disposed and extending between the top surface and the bottom surface, an aperture defined between an end portion of the top surface and an adjacent end portion of a sidewall, the aperture configured to receive the blade, a top skin facing surface comprising the top surface and the blade, and a hydrophobic coating layer disposed on at least a portion of the top skin facing surface.

Clause 2. The surgical clipper blade assembly of clause 1, wherein the hydrophobic coating layer is made of polytetrafluoroethene (PTFE) or perfluoroalkoxy polymer resin (PFA).

Clause 3. The surgical clipper blade assembly of clause 1 or 2, wherein the blade comprises a plurality of blade edges and is made of stainless steel, and the top surface, the bottom surface, and the plurality of sidewalls are made of ABS plastic.

Clause 4. The surgical clipper blade assembly of any of clauses 1 to 3, wherein the portion of the top skin facing surface comprises the top surface, the blade, or both.

Clause 5. The surgical clipper blade assembly of any of clauses 1 to 4, further comprising a plurality of ribs in a rib pattern configuration disposed on the top surface, and the top skin facing surface comprises the plurality of ribs.

Clause 6. The surgical clipper blade assembly of any of clauses 1 to 5, wherein the portion of the top skin facing surface comprises the plurality of ribs.

Clause 7. The surgical clipper blade assembly of any of clauses 1 to 6, wherein the portion of the top skin facing surface comprises at least one of the top surface, the blade, the plurality of ribs, or combinations thereof.

Clause 8. In another embodiment, a surgical clipper blade assembly may include a blade configured to remove hair from a skin area, a top surface, a bottom surface, a plurality of sidewalls disposed and extending between the top surface and the bottom surface, an aperture defined between an end portion of the top surface and an adjacent end portion of a sidewall, the aperture configured to receive the blade, a plurality of ribs in a rib pattern configuration disposed on the top surface, a top skin facing surface comprising the top surface, the blade, and the plurality of ribs, and a hydrophobic coating layer disposed on at least a portion of the top skin facing surface.

Clause 9. The surgical clipper blade assembly of clause 8, wherein the hydrophobic coating layer is made of polytetrafluoroethene (PTFE) or perfluoroalkoxy polymer resin (PFA).

Clause 10. The surgical clipper blade assembly of clause 8 or 9, wherein the portion of the top skin facing surface comprises one or more surfaces of the plurality of ribs.

Clause 11. The surgical clipper blade assembly of any of clauses 8 to 10, wherein the portion of the top skin facing surface comprises top surfaces of the plurality of ribs.

Clause 12. The surgical clipper blade assembly of any of clauses 8 to 11, wherein the portion of the top skin facing surface comprises the top surface, the blade, the plurality of ribs, or combinations thereof.

Clause 13. In yet another embodiment, a method of using a surgical clipper blade assembly for hair removal from a skin area of a patient may include coupling the surgical clipper blade assembly to a body of a surgical clipper. The surgical clipper blade assembly may include a blade, a top surface, a bottom surface, a plurality of sidewalls disposed and extending between the top surface and the bottom surface, an aperture configured to receive the blade and defined between an end portion of the top surface and an adjacent end portion of a sidewall, and a hydrophobic coating layer disposed on at least a portion of a top skin facing surface comprising the top surface and the blade. The method may further include facing the top skin facing surface toward the skin area, and operating the blade through the body to remove hair from the skin area of the patient such that the hydrophobic coating layer reduces friction forces during blade operation and prevents risk of skin abrasions during blade operation.

Clause 14. The method of clause 13, wherein the hydrophobic coating layer is made of polytetrafluoroethene (PTFE) or perfluoroalkoxy polymer resin (PFA).

Clause 15. The method of clause 13 or clause 14, wherein the portion of the top skin facing surface comprises the top surface, the blade, or both.

Clause 16. The method of any of clauses 13 to 15, wherein the surgical clipper blade assembly further includes a plurality of ribs in a rib pattern configuration disposed on the top surface, and the top skin facing surface comprises the plurality of ribs.

Clause 17. The method of clause 16, wherein the portion of the top skin facing surface comprises the plurality of ribs, the top surface, the blade, or combinations thereof.

Clause 18. The method of any of clauses 13 to 16, wherein the body of the surgical clipper is configured to electronically operate the blade and comprises an enclosure including an electrical motor and a battery, the battery configured to be rechargeable through coupling of the body to a charging adaptor.

Clause 19. The method of any of clauses 13 to 18, wherein the body of the surgical clipper further comprises a charge indicator configured to indicate a low battery level below a predefined threshold.

Clause 20. The method of any of clause 20, further comprising triggering an alarm through the charge indicator of the low battery level, coupling the body to the charging adaptor, and recharging the battery.

For the purposes of describing and defining the present disclosure, it is noted that recitations herein of "at least one" component, element, etc., should not be used to create an inference that the alternative use of the articles "a" or "an" should be limited to a single component, element, etc.

It is noted that recitations herein of a component of the present disclosure being "configured" in a particular way, to embody a particular property, or to function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

For the purposes of describing and defining the present disclosure it is noted that the terms "substantially" and "approximately" and "about" are utilized herein to represent the inherent degree of uncertainty that may be attributed to any quantitative comparison, value, measurement, or other representation. The terms "substantially" and "approximately" and "about" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A surgical clipper blade assembly comprising:
   a blade configured to remove hair from a skin area;
   a top surface;
   a bottom surface;
   sidewalls disposed and extending between the top surface and the bottom surface;
   an aperture adjacent the top surface, the aperture configured to receive the blade; and
   a plurality of ribs in a rib pattern configuration disposed on the top surface;
   wherein the plurality of ribs defines a top skin facing surface and only the top skin facing surface of the plurality of ribs is coated by a hydrophobic coating layer such that the top surface adjacent the plurality of ribs is uncoated by the hydrophobic coating layer;
   wherein the plurality of ribs comprises a curved rib that is located in at least one outboard region of the top surface and that curves inward, away from one of the sidewalls.

2. The surgical clipper blade assembly of claim 1, wherein the hydrophobic coating layer is made of polytetrafluoroethene (PTFE) or perfluoroalkoxy polymer resin (PFA).

3. The surgical clipper blade assembly of claim 1, wherein:
   the blade comprises a plurality of blade edges and is made of stainless steel; and
   the top surface, the bottom surface, and the sidewalls are made of ABS plastic.

4. A surgical clipper blade assembly comprising:
   a blade configured to remove hair from a skin area;
   a top surface;
   a bottom surface;
   a plurality of sidewalls disposed and extending between the top surface and the bottom surface;
   an aperture adjacent the top surface, the aperture configured to receive the blade;
   a plurality of ribs in a rib pattern configuration disposed on the top surface, wherein the plurality of ribs defines a top skin facing surface; and
   a hydrophobic coating layer disposed only on the top skin facing surface of the plurality of ribs such that the top surface adjacent the plurality of ribs is uncoated by the hydrophobic coating layer,
   wherein the plurality of ribs comprises a curved rib that is located in at least one outboard region of the top surface and that curves inward, away from one of the sidewalls.

5. The surgical clipper blade assembly of claim 4, wherein the hydrophobic coating layer is made of polytetrafluoroethene (PTFE) or perfluoroalkoxy polymer resin (PFA).

6. A method of using a surgical clipper blade assembly for hair removal from a skin area of a patient, the method comprising:
   coupling the surgical clipper blade assembly to a body of a surgical clipper, the surgical clipper blade assembly including a blade, a top surface, a bottom surface, sidewalls disposed and extending between the top surface and the bottom surface, an aperture configured to receive the blade and adjacent, and a hydrophobic coating layer disposed only on a top skin facing surface formed by a plurality of ribs on the top surface such that the top surface adjacent the plurality of ribs is uncoated by the hydrophobic coating layer;
   facing the top skin facing surface toward the skin area; and
   operating the blade through the body to remove hair from the skin area of the patient such that the hydrophobic coating layer reduces friction forces during blade operation and prevents risk of skin abrasions during blade operation;
   wherein the plurality of ribs comprises a curved rib that is located in at least one outboard region of the top surface and that curves inward, away from one of the sidewalls.

7. The method of claim 6, wherein the hydrophobic coating layer is made of polytetrafluoroethene (PTFE) or perfluoroalkoxy polymer resin (PFA).

8. The method of claim 6, wherein the body of the surgical clipper is configured to electronically operate the blade and comprises an enclosure including an electrical motor and a battery, the battery configured to be rechargeable through coupling of the body to a charging adaptor.

9. The method of claim 8, wherein the body of the surgical clipper further comprises a charge indicator configured to indicate a low battery level below a predefined threshold.

10. The method of claim 9, further comprising:
    triggering an alarm through the charge indicator of the low battery level;
    coupling the body to the charging adaptor; and
    recharging the battery.

* * * * *